US010645756B2

(12) United States Patent
Yu et al.

(10) Patent No.: US 10,645,756 B2
(45) Date of Patent: May 5, 2020

(54) HEATER, USE THEREOF AND METHOD FOR PREPARING ISOCYANATE USING HEATER

(71) Applicant: Wanhua Chemical Group Co., Ltd., Yantai (CN)

(72) Inventors: Yong Yu, Yantai (CN); Yonghua Shang, Yantai (CN); Zhongping Sun, Yantai (CN); Xuelei Cui, Yantai (CN); Peng Wang, Yantai (CN); Zhengao Lv, Yantai (CN); Weiqi Hua, Yantai (CN)

(73) Assignee: Wanhua Chemical Group Co., Ltd. (CN)

( * ) Notice: Subject to any disclaimer, the term of this patent is extended or adjusted under 35 U.S.C. 154(b) by 283 days.

(21) Appl. No.: 15/309,705

(22) PCT Filed: Jun. 16, 2014

(86) PCT No.: PCT/CN2014/079948
§ 371 (c)(1),
(2) Date: Nov. 8, 2016

(87) PCT Pub. No.: WO2015/188389
PCT Pub. Date: Dec. 17, 2015

(65) Prior Publication Data
US 2017/0164424 A1  Jun. 8, 2017

(30) Foreign Application Priority Data

Jun. 10, 2014  (CN) .......................... 2014 1 0254831

(51) Int. Cl.
*F16L 53/38*  (2018.01)
*C08G 18/08*  (2006.01)
(Continued)

(52) U.S. Cl.
CPC ........... *H05B 1/0244* (2013.01); *B01B 1/005* (2013.01); *B01D 1/0017* (2013.01); *B01D 1/14* (2013.01);
(Continued)

(58) Field of Classification Search
CPC ....... F16L 53/38; C08G 18/08; C08G 18/727; B01D 1/14; H05B 3/00; H05B 1/0244; B01B 1/005; B01B 1/0017
See application file for complete search history.

(56) References Cited

U.S. PATENT DOCUMENTS 1,484,616 A    2/1924   Aske
3,781,528 A *  12/1973  Schrewelius ............ H05B 3/22
                                                    219/468.1
(Continued)

FOREIGN PATENT DOCUMENTS

CN     101912751 A    12/2010
CN     102471242 A    5/2012
(Continued)

OTHER PUBLICATIONS

Supplementary European Search Report for EP 14 89 4274 (PCT/CN2014079948) dated Dec. 21, 2017.
(Continued)

*Primary Examiner* — Ibrahime A Abraham
*Assistant Examiner* — John J Norton
(74) *Attorney, Agent, or Firm* — Lerner, David, Littenberg, Krumholz & Mentlik, LLP

(57) ABSTRACT

A heater for heating and vaporizing droplets in gas stream, comprising a heater housing and a heater body located inside the heater housing, wherein the heater housing is provided with an airflow inlet and an airflow outlet, the airflow enters into the heater housing via the airflow inlet, flows through the heater body, and then is discharged via the airflow outlet;

(Continued)

the heater body comprises a stereoscopic network structure formed by interweaving one or more electrical heating wires. The use of the heater and a method for preparing isocyanate using the heater. The heater has a simple structure, a low pressure loss, uniform heating and a high heat utilization ratio during preparing isocyanate.

7 Claims, 1 Drawing Sheet

(51) Int. Cl.
    *C08G 18/72*     (2006.01)
    *H05B 3/00*     (2006.01)
    *B01D 1/00*     (2006.01)
    *B01B 1/00*     (2006.01)
    *B01D 1/14*     (2006.01)
    *H05B 1/02*     (2006.01)

(52) U.S. Cl.
    CPC ........... *C08G 18/08* (2013.01); *C08G 18/727* (2013.01); *F16L 53/38* (2018.01); *H05B 3/00* (2013.01)

(56) References Cited

U.S. PATENT DOCUMENTS

| | | | |
|---|---|---|---|
| 4,203,838 A * | 5/1980 | Shimizu | B01D 53/34 210/603 |
| 4,424,680 A * | 1/1984 | Rothchild | B01D 5/0027 62/46.1 |
| 6,181,874 B1 * | 1/2001 | Ireland | F24H 1/103 392/398 |
| 2008/0216655 A1 * | 9/2008 | Vimalchand | B01D 45/12 95/271 |
| 2012/0108845 A1 * | 5/2012 | Bruns | C07C 263/10 560/347 |
| 2012/0111315 A1 * | 5/2012 | Grenda | F23K 5/22 126/344 |

FOREIGN PATENT DOCUMENTS

| | | |
|---|---|---|
| CN | 103201002 A | 7/2013 |
| CN | 103398262 A | 11/2013 |
| EP | 1935876 A1 | 6/2008 |
| JP | S49140743 U | 12/1974 |
| JP | H01206591 A | 8/1989 |
| JP | H07218145 A | 8/1995 |
| JP | 2006225182 A | 8/2006 |
| JP | 2012238415 A * | 12/2012 |
| JP | 2012238415 A | 12/2012 |
| JP | 2012532159 A | 12/2012 |
| JP | 2012533525 A | 12/2012 |
| KR | 20100116170 A | 10/2010 |
| KR | 20120038443 A | 4/2012 |
| WO | 9708918 A1 | 3/1997 |

OTHER PUBLICATIONS

International Search Report for Application No. PCT/CN2014/079948 dated Feb. 27, 2015.

* cited by examiner

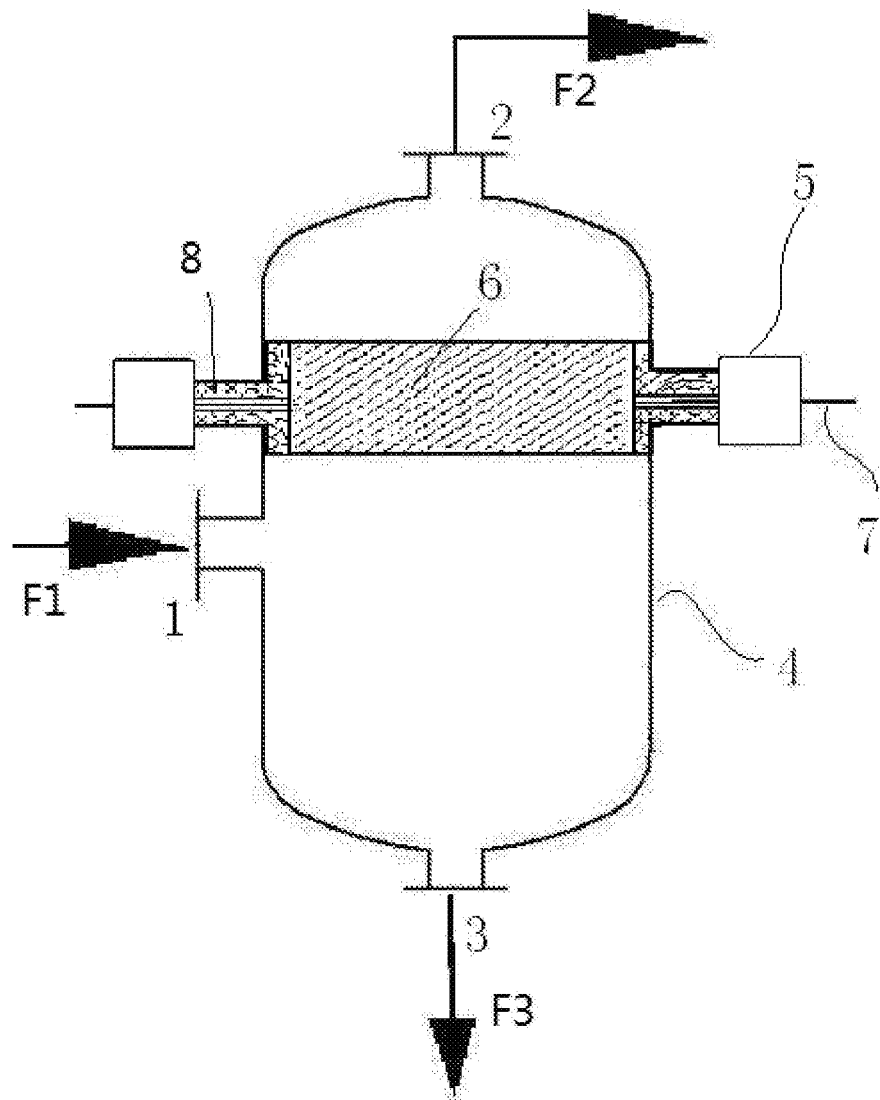

HEATER, USE THEREOF AND METHOD FOR PREPARING ISOCYANATE USING HEATER

CROSS REFERENCE TO RELATED APPLICATIONS

The present application is a national phase entry under 35 U.S.C. § 371 of International Application No. PCT/CN2014/079948, filed Jun. 16, 2014, which claims priority from Chinese Patent Application No. 201410254831.1, filed Jun. 10, 2014, all of which are hereby incorporated herein by reference.

TECHNICAL FIELD

The present invention relates to a heater, the heater is used for heating and vaporizing droplets contained in gas stream, and the present invention also relates to a method for preparing isocyanate using the heater.

TECHNICAL BACKGROUND

The method for preparing isocyanate by primary amine and phosgene in gas phase is well known. In the method, primary amine enters into a gas phase phosgenation reactor after vaporization, and reacts with phosgene to produce isocyanate. The effect of vaporization of primary amine has a significant influence to the reaction product.

In the real industrial production operation, the problem of incomplete vaporization appears frequently during the vaporization of primary amine, and amine droplets that are not vaporized present in the amine gas stream formed after vaporization. These amine droplets will enter into the gas phase phosgenation reactor with the amine gas stream and cause unfavorable consequences if no corresponding measures are taken to remove them. In one aspect, as the diameters of the amine droplets are relatively large and the droplets are heated unevenly, the amine molecules on the surface of the droplets will react with the phosgene to produce isocyanates, while under high temperature the amine molecules inside the droplets will be carbonized to produce carbon deposit and ammonia gas, and the ammonia gas will react with hydrogen chloride (one of the products of the reaction of amine and phosgene) to produce solid ammonium chloride, and the carbon deposit and ammonium chloride will easily cause the blocking of the reactor and pipes, thus frequently cleaning up will be needed, the running periods of the device will be shortened. In another aspect, undesired side reactions often happen between the amine molecules inside these droplets and the isocyanates produced on the surface of the droplets, resulting in the increase of heavy component impurities in the reaction product and the decrease of yield.

At present, there are two methods for removing the amine droplets contained in the amine gas stream. The first method is to remove droplets by gas-liquid separation, generally, with a relative large pressure loss in this method. The second method is to let amine droplets vaporize by heating to obtain amine gas stream that does not contain amine droplets. However, the present heating method has the disadvantages of large pressure loss and unevenly heating. During the removing of amine droplets in the amine gas stream, if the pressure loss is too large, the pressure during amine vaporization will be increased, and there will be a rise of the temperature for vaporization, which will cause amine to decompose thus produce ammonia gas. The ammonia gas produced enters into the phosgenation reactor then reacts with the hydrogen chloride (one of the products of the reaction of amine and phosgene) to produce solid ammonium chloride, which will easily cause the blocking of the reactor inner wall and pipes, and the running periods of the device will be shortened. If the heating method is used, there may be the problem of unevenly heating, which will easily cause the circumstance that the heating temperature is too high or too low locally, and even cause the circumstance that the heating temperature of some parts is too high while the temperature of other parts is too low. When the heating temperature is too high locally, the amine molecules in the amine droplets will be carbonized during the removing of amine droplets, which leads to the formation of carbon deposit and ammonia gas thus blocking the device; when the heating temperature is too low locally, some of the amine molecules react with the obtained isocyanates to produce heavy component impurities as they cannot reach the temperature required for the phosgenation reaction after the amine gas stream enters into the phosgenation reactor.

In EP1935876A1, amine gas streams that contain basically no droplets are generated before entering into the reactor, which makes the continuous running period of the reactor increase significantly. The patent document mentioned that the removal of amine droplets in amine gas stream can be performed in a droplet separator provided between the amine vaporization system and the overheating system, and/or by using a vaporization device with the function of droplet removal itself, and it is mentioned that the droplet remover with less pressure loss is preferred. However, said method is disadvantageous for large scale industrialization of the gas phase phosgenation reaction, as the pressure loss of the droplet separator will dramatically increase with the increase of volume flow rate. Under the same pressure loss, the separation rate of the amine droplets of the droplet separator under high volume flow rate is lower than that under low volume flow rate, therefore the effect of removing amine droplet is worse. If the separation rate of the amine droplets of the droplet separator is increased by means of increasing the pressure loss, the pressure during amine vaporization will be increased, thus causing the above mentioned blocking of the device, and shortening the running period of the device.

CN102471242A provides a method for removing droplets that are not vaporized after the vaporization of amine. Said method allows a small amount of droplets-containing amine that obtained after the removal of most of the droplets of the vaporized amine gas stream by the droplet separator or not by the droplet separator to be overheated in the inlet pipe of the guide reactor, and it is required for the residence time of the overheating process to be longer than 0.01 second to promote the vaporization of the contained droplets, thus finally forming a completely vaporized flow. The overheating of the vaporized amine gas stream in the inlet pipe can be performed in a device such as a tube bundle heat exchanger or a heating pipe. But during the actual operation process, if droplet separator is used, there will be large pressure loss, and the blocking of the device and the shortening of the running period of the device mentioned above will be caused. If the vaporized amine gas stream is overheated directly inside the inlet pipe, instead of using droplet separator, as the temperature of the material close to the pipe wall of the inlet pipe is much higher than that of the center of the pipe, the vaporized amine gas stream will be unevenly heated, and the amine molecules inside the amine droplets in the amine gas stream close to the pipe wall under high temperature will be carbonized to produce carbon deposit and ammonia gas. While the temperature of the amine gas stream in the center of the pipe is low, thus it will produce heavy component impurities after entering into the phosgenation reactor. In addition, the inlet pipe for overheating must be longer than ever in order for the amine droplets in the amine gas stream to be sufficiently vaporized. The residence time of the amine gas stream under high temperature is prolonged, which will easily cause the decomposition of the amine to produce ammonia gas, and consequently more ammonium chloride will be formed in the reactor. Thus the blocking of the downstream devices will be accelerated, and the running period of the devices will be shortened.

CN101912751A discloses an amine vaporizer that is made of inert inorganic conductive material, wherein the inert inorganic conductive material possesses irregular microporous channels. Liquid amine enters into the amine vaporizer to vaporize after it is atomized and dispersed into droplets. The vaporizer is used for the vaporization of the amine droplets obtained via atomization, not for the removing of the amine droplets contained in the amine gas stream obtained via vaporization. Even if the vaporizer is used as the heater for the removing of the amine droplets contained in the amine gas stream, the pressure loss generated during the vaporization of the amine droplets will be large, which will easily cause the blocking of the devices and the shortening of the running period of the devices mentioned above, since a microporous channel structure is used as the main body of the vaporizer, which has long channels and low porosity.

In addition, the droplet size of the droplets in the amine gas stream generated during the amine vaporization is generally between 0.1 mm and 1 mm. In conditions where the effect of vaporization is poor, droplets with a droplet size between 1 mm and 2 mm will appear. The larger the droplet size, the longer the time needed to vaporize and heat the droplets, and heating under high temperature for long time will cause the amine to decompose thus result in the above undesired result.

Therefore, during the process of preparing isocyanate by gas phase phosgenation, a device for removing the amine droplets in the amine gas stream is needed, with low pressure loss or basically no pressure loss, and evenly heating.

SUMMARY OF THE INVENTION

One of the objects of the present invention is to provide a heater to eliminate the amine droplets that are not vaporized in the amine gas stream after the vaporization of amine in the process of preparing isocyanate. The heater has a simple structure, low pressure loss and high energy utilization ratio, and the amine gas stream may be heated evenly via the heater.

Another object of the present invention is use of the heater for the vaporization and heating of the droplets in the gas stream.

Again another object of the present invention is to provide a method for preparing isocyanate using the heater. In the method, amine droplets contained in the amine gas stream after amine vaporization can be eliminated. The pressure loss in the process is low, the heat utilization ratio is high, the temperature in every part of the amine gas stream is homogeneous, and the effect of the subsequent gas phase phosgenation is increased effectively.

In order to achieve the above objects, the following technical solutions are used in the present invention:

A heater for heating and vaporizing droplets in gas stream, comprising a heater housing and a heater body located inside the heater housing, wherein the heater housing is provided with an airflow inlet and an airflow outlet, the airflow enters into the heater housing via the airflow inlet, flows through the heater body, and then is discharged via the airflow outlet; the heater body comprises a stereoscopic network structure formed by interweaving one or more electrical heating wires.

Preferably the gas stream is an amine gas stream, and the droplets are amine droplets, i.e. the heater is used for the heating and vaporizing amine droplets in the amine gas stream.

The heater body with a stereoscopic network structure formed by interweaving electrical heating wires is used in the present invention. When the heater is used, the amine gas stream that contains amine droplets flows through the heater body inside the heater housing. The amine droplets in the amine gas stream contact directly with the electrical heating wires and are vaporized. The energy utilization ratio of the heater can reach above 95%, even above 99%. As stereoscopic structure is used, the pressure loss is low, thus the pressure and temperature in the amine vaporizer that is used for the vaporization of amine are both low, and amine will not be decomposed easily. Therefore, the formation of solid ammonium chloride in the amine vaporizer and the blocking of device could be avoided, and the running period of the device is prolonged. Meanwhile, the temperature difference of the electrical heating wires of the stereoscopic network structure is small, which allows for evenly heating of the amine droplets, avoiding the heating temperature to be too high or too low locally.

The heater can be a vertical type heater or a horizontal type heater.

Preferably, the heater is a vertical type heater, amine airflow inlet is located on the heater housing below the heater body; and amine airflow outlet is located on the heater housing above the heater body, more preferably located on the top of the heater housing.

The shape of the heater body matches with that of the heater housing. Preferably, the heater body and the heater housing are all in the forms of cylinder shapes.

Preferably, the stereoscopic network structure formed by interweaving electrical heating wires is combined with the inner wall of the heater housing through sealing insulation packing to avoid the circumstance of short circuit during the working of the heater.

The sealing insulation packing can be a part of the heater body, or can be a part of the heater housing, or can be an individual component part of the heater, to combine the stereoscopic network structure with the inner wall of the heater housing.

Preferably, the sealing insulation packing comprises but is not limited to polyester, polycarbonate, PVC sleeve pipe, silicone rubber, polyethylene, polyvinyl chloride and so on.

As a preferred embodiment of the present invention, the heater body comprises one stereoscopic network structure.

When the heater body comprises multiple stereoscopic network structures, preferably, each stereoscopic network structure is arranged parallel in the height direction of the heater body, and the adjacent network structures are closely contacted or separated. With such design, the number of the network structures can be adjusted flexibly according to the actual requirement of production, thus the height of the heater body will be adjusted, and the heating area of the heater body and the pressure drop inside the heater will be adjusted accordingly.

The height-to-diameter ratio of the heater body can be determined according to the actual need for heating. Preferably, the height-to-diameter ratio of the heater body is 1:0.01-100, more preferably 1:0.1-10, further preferably 1:1-10. When any of the above height-to diameter ratios is used, the pressure drop of the heater will be low while the heating requirement is satisfied by the heater body.

It is important to note that when multiple stereoscopic network structures are used by the heater body, the height-to-diameter ratio of the heater body is the ratio of the sum of the heights of each stereoscopic network structure to the diameter.

The stereoscopic network structure can be formed by regular or irregular ways of interweaving electrical heating wires, preferably irregular ways; the mesh of the stereoscopic network structure can be a regular or irregular shape, preferably irregular shape.

Preferably, the cross section of the electrical heating wire is a convex polygon shape, a sector shape or an arch shape.

The cross section of the electrical heating wire is the section perpendicular to the length direction of the electrical heating wire.

The arch shape is the shape formed by a chord of a circle and the arc opposite the chord.

The sector shape is the shape formed by an arc of a circle and the two radiuses that pass the two ends of the arc.

When the above shapes are used as the cross section of the electrical heating wires, sharp edges are maintained for electrical heating wires, and amine droplets will be cut into smaller droplets effectively while contacting the wires during the process of flowing. Thus the time of vaporization will be shortened, and the efficiency of vaporization will be increased. Meanwhile, the shortening of the vaporization time will also effectively avoid the decomposition of amine caused by long time heating of amine droplets under high temperature. Moreover, the amine droplets are cut into smaller droplets, which avoids the carbonation of the amine molecules inside the droplets under high temperature to produce carbon deposit and ammonia gas because the droplet size of the amine droplets are too large.

Preferably, the above shapes are used by the electrical heating wires of the heater body, and the amine droplets in the amine gas stream will be cut into droplets with droplet size smaller than 0.5 mm, preferably smaller than 0.25 mm, more preferably smaller than 0.1 mm when passing through the heater body.

Preferably, the cross section of the electrical heating wire is a convex polygon shape which has a smallest angle or two smallest angles that are equal, the angularity of the smallest angle is smaller than 90°, preferably 1° to 15°, more preferably 1° to 5°.

When the above angularities of the smallest angle are used, the edges of the electrical heating wires are extremely sharp, which is advantageous for the cutting of the amine droplets into smaller droplets.

Preferably, the electrical heating wires are configured such that the smallest angle of the convex polygon shape is opposite to the flowing direction of the amine gas stream inside the heater housing, and the bisector of the smallest angle intersects with or is paralleled with, preferably is paralleled with the flowing direction of the amine gas stream inside the heater housing. With such configuration, amine gas stream will directly pass through the sharp edges of the electrical heating wires, and the amine droplets will effectively be cut into smaller droplets.

Preferably, the number of the sides of the convex polygon is 3-100, preferably 3-20, more preferably 3-10, further preferably 3-5.

Preferably, the cross section of the electrical heating wire is an arch shape, the central angle corresponding to the arc of the arch is smaller than 180°, preferably 1° to 30°, more preferably 1° to 10°.

Preferably, the cross section of the electrical heating wire is a sector shape, the central angle of the sector is smaller than 90°, preferably 1° to 15°, more preferably 1° to 5°. When the above central angles are used, the edges of the central angle of the electrical heating wires will be extremely sharp, which is advantageous for the cutting of the amine droplets into smaller droplets.

Preferably, the electrical heating wires are configured such that the central angle of the sector is opposite to the flow direction of the amine gas stream inside the heater housing, and the bisector of the central angle intersects with or is paralleled with, preferably is paralleled with the flowing direction of the amine gas stream inside the heater housing. With such configuration, amine gas stream will directly pass through the sharp edges of the electrical heating wires, which is advantageous for the large amine droplets to be cut into smaller droplets.

Those skilled in the art may understand that the electrical heating wires that compose the heater body should be exposed to the flow direction of the amine gas stream as much as possible to effectively cut the amine droplets in the amine gas stream.

Preferably, the hydraulic diameter of the mesh of the stereoscopic network structure is smaller than 1 nm, preferably 0.01-0.5 mm, more preferably 0.01-0.25 mm.

Preferably, the porosity of the stereoscopic network structure is 75-99.5%, preferably 90-99.5%.

Preferably, the heat exchange area per unit volume of the stereoscopic network structure is 100-1000 $m^2/m^3$.

Preferably, the bottom of the heater housing is provided with a drain port.

Generally, the content of amine droplets in the amine gas stream that is vaporized in the amine vaporizer is low, and the amine droplets can be completely vaporized by the heating of the heater of the present invention. But some of the amine vaporizers have poor vaporizing effect, for example, the content of amine droplets in the amine gas stream can be above 20 wt %. When such amine gas stream is heated by the heater of the present invention, a part of the amine droplets that are not vaporized will be separated from the amine gas stream, and will be combined into a flow and drop, then the flow will be discharged from the drain port at the bottom of the heater. This part of liquid amine can return to the amine vaporizer to revaporize to increase the vaporization rate.

Preferably, the electrical heating wires are made of inert inorganic nonmetallic materials that are conductive. The inert inorganic nonmetallic materials can be doped with metals or are not doped with metals.

Preferably, the inert inorganic nonmetallic materials are doped with different contents of metals, such as the materials can be doped with 1-15 wt %, preferably 2-10 wt % metals. The electrical resistivity of the material is controlled by adjusting the content of the doped metals.

The heater bodies with different conductive characteristics can be obtained by the control of the electrical resistivity of the materials. Normally, the inert inorganic nonmetallic materials doped with metals have relatively low electrical resistivity, such as 1-5000 Ω·m, disclosed in the Chinese patent application CN1962544A. Even under the circumstance that the voltage of the additional power supply becomes lower (6V-24V), a working mechanism that a large current can still be obtained under a low voltage can be formed, which in one aspect ensure the power of the heater body, in another aspect, ensure a safe operation of the device.

Preferably, the inert inorganic nonmetallic materials are selected from one or two or more of molybdenum disilicide, lanthanum chromate, ceramic, silicon carbide and tin oxides; the metals doped with the inert inorganic nonmetallic materials are selected from one or two or more of Ti, Ni, Fe, W, Mo, V, Al, Cu and Zn.

In the reactor of the present invention, a certain voltage is applied to the heater body by an external power source, the temperature of the heater body will be increased gradually as the corresponding current is generated, and a certain temperature will be reached. The temperature and power of the heater body are controlled by adjusting the voltage of the external power source.

When the heater body comprises a plurality of stereoscopic network structures, each of the stereoscopic network structures can be connected in parallel by wires, and applied with voltage by an external power source.

Preferably, the voltage of the external power source is 3-36V, preferably 6-24V. It can be ensured that the electrical heating wires can reach a certain temperature when the voltage is higher than 3V. The security threats in operation can be avoided when the voltage is lower than 24V.

There is no special requirement for the type of an external power source and its connection to the heater body, as long as the external power source can provide voltage to the heater body to generate heat. In a preferred embodiment of the present invention, an external power source applies voltage to the heater body via an electrode lead. The electrode lead passes through the heater housing and the sealing insulation packing between the heater housing and the heater body to connect with the heater body, and sealing fastening nut is provided between the electrode lead and the heater housing to form an insulation between the electrode lead and the heater housing.

The material of the heater housing is preferably the stainless steel that is easy to be processed and does not have any affect to the gas phase phosgenation reaction, such as 316, 316 L, 304 and dual-phase steel and so on.

Preferably, a thermal insulation layer is provided outside the heater housing to decrease the loss of heat during the working of the heater.

Preferably, the thermal insulation materials of the thermal insulation layer are selected from one or more of composite silicate cotton, rock wool or aluminum silicate needle-felted carpet.

Preferably, the thickness of the thermal insulation layer is 10-20 mm.

The present invention also provides use of the heater for eliminating of droplets in the gas stream, especially for eliminating of amine droplets in the amine gas stream.

The present invention also provides a method for preparing isocyanate, comprising:
(1) vaporizing amine into amine gas stream that contains amine droplets;
(2) eliminating the amine droplets contained in the amine gas stream to obtain amine gas stream that almost does not contain amine droplets;
(3) allowing the gas phase phosgenation reaction to be carried out between the amine gas stream that almost does not contain amine droplets and phosgene to obtain isocyanate;

wherein in step (2), the heater of the present invention is used to eliminate the amine droplets in the amine gas stream.

Preferably, the pressure loss in the heater in step (2) is lower than 5 kPa, preferably lower than 2 kPa, more preferably lower than 1 kPa.

Preferably, the temperature difference between any two or more points on the surface of the electrical heating wires of the heater body in step (2) is lower than 1° C., preferably lower than 0.2° C.

Preferably, the amine droplets that are not vaporized in step (2) are cut into droplets with droplet size less than 0.5 mm, preferably less than 0.25 mm, more preferably less than 0.1 mm by the electrical heating wires.

The amine in the present invention is one or two or more of aromatic and aliphatic primary amine, preferably one or two or more of toluenediamine (TDA), methylene diphenylamine (MDA), 1,6-hexanediamine (HDA), isophorone diamine (IPDA), dicyclohexylmethane diamine ($H_{12}MDA$), phenylenediamine, naphthylenediamine, 1,4-butanediamine, 1,8-octanediamine, 1,10-decanediamine, 1,12-dodecanediamine, 1,5-pentanediamine, tetramethyl benzene dimethylene diamine, cyclohexanediamine and methyl cyclohexane diamine and so on.

The "amine gas stream that almost does not contain amine droplets" in steps (2) and (3) is the amine gas stream where the content of amine droplets is lower than 0.1 wt %, preferably the amine gas stream that does not contain amine droplets.

Preferably, step (1) further comprises the step of preheating amine before the vaporization of amine.

Preferably, step (1) further comprises the step of mixing inert medium with amine before the vaporization of amine or the step of adding inert medium to the amine gas stream obtained after the vaporization of amine, to decrease the partial pressure.

The inert medium is selected from inert gases and/or vapor of inert solutions. The inert gases are selected from one or two or more of nitrogen, argon, helium and carbon dioxide. The inert solutions are halogen substituted or unsubstituted aromatic hydrocarbon, such as one or two or more of toluene, dimethylbenzene, chlorobenzene and o-dichlorobenzene. The inert medium is preferably nitrogen. Preferably, the molar ratio of the inert medium to amine is 1-10:1, more preferably 1.5-4:1.

The amine vaporizer in step (1) is not limited to plate type evaporators, falling-film evaporators, central circulating tube type evaporators, shell and tube type evaporators, dry tube type evaporators, laminated evaporators or film evaporators etc., and liquid atomization devices such as atomizing spray nozzle can also be used.

Preferably, the molar ratio of phosgene to amine in step (3) is 2-25:1, preferably 4-20:1.

Preferably, the gas product obtained after the reaction of phosgene and amine is condensed and absorbed to obtain isocyanate reaction liquid which is further separated to obtain isocyanate product.

The pressure loss mentioned in the present invention is the pressure difference between the outlet of the amine vaporizer and the inlet of the gas phase phosgenation reactor. When the heater of the present invention is used, since the outlet of the amine vaporizer is connected to the amine gas stream inlet of the heater, and the outlet of the amine gas stream of the heater is connected to the inlet of the gas phase phosgenation reactor, therefore, the pressure loss is actually the pressure drop inside the heater.

In the method for preparing isocyanate of the present invention, as the process of removing amine droplets in the amine gas stream by the heater is contained in the present invention, therefore, the requirement of the vaporization rate of amine in step (1) is not as high as that in a conventional process, thus allowing for relative mild conditions for amine vaporization in step (1). Amine decomposition doesn't happen easily in the process of amine vaporization, and the formation of solid amine chloride in step (3) could be prevented.

In addition, the heater body of the heater of the present invention has the advantage of homogeneous heating temperature, thus allowing the amine gas stream to have homogeneous temperature after eliminating of the amine droplets, avoiding the amine carbonation reaction caused by the overheat of the amine droplets locally, or avoiding the condition that the temperature of the amine gas stream is too low locally, which cannot reach the temperature required for the gas phase phosgeneation, thus the amine is reacted with the obtained isocyanate to produce heavy component.

BRIEF DESCRIPTION OF THE DRAWINGS

FIG. 1 is a schematic view of a preferred embodiment of the heater of the present invention, wherein,
1—inlet of amine gas stream, 2—outlet of amine gas stream, 3—drain port, 4—heater housing, 5—sealing fastening nut, 6—heater body, 7—electrode leads, 8—sealing insulation packing, F1—amine gas stream with droplets that are not vaporized, F2—amine gas stream without droplets, F3—discharged liquid material.

DETAILED DESCRIPTION

The heater and the method for preparing isocyanate using the heater of the present invention are further illustrated below; however, the present invention is not limited to the following examples.

Example 1

A preferred embodiment of the heater of the present invention is shown in FIG. 1. The heater is a vertical tank that comprises a cylinder heater housing 4 and a cylinder heater body 6 that is provided inside the heater housing 4. The diameter of the heater body 6 is slightly smaller than that of the heater housing, and sealing insulation packing 8 is provided between the heater body 6 and the heater housing 4. An amine gas stream inlet 1 is provided on the side wall of the heater housing 4, an amine gas stream outlet 2 is provided on the top of the heater housing 4, and a drain port 3 is provided at the bottom of the heater housing 4. An external power source (not shown) applies a voltage to the heater body 6 through electrode leads 7, and controls the power and heating temperature of the heater body 6 through adjusting the voltage of the power source. A sealing fastening nut 5 is provided between the electrode leads 7 and the heater housing 4 to insulate the electrode leads 7 and the heater housing 4.

The heater body 6 is composed of a stereoscopic network structure that is formed by interweaving electrical heating wears and the thickness of the network structure is 15 cm, the diameter is 40 cm.

The heater body 6 is a stereoscopic network structure that is formed by irregularly interweaving electrical heating wires, and the meshes are of irregular shapes. The electrical heating wires are made of inert silicon carbide conductive materials that are doped with 2 wt % Ni. The cross sections of the electrical heating wires are sector shapes with the central angularity of 10°.

When the heater is used to eliminate the amine droplets that are not vaporized in the amine gas stream, the amine gas stream F1 that contained the droplets that are not vaporized enters into the heater housing 4 via the amine gas stream inlet 1, When the amine gas stream passes through the heater body 6, the amine droplets are cut into smaller droplets by the electrical heating wires, which are heated and vaporized by the electrical heating wires, and then discharged from the heater via the amine gas stream outlet 2. Thus, amine gas stream that basically does not contain amine droplets F2 is obtained, which enters into the subsequent phosgenation reactor to react with phosgene to obtain isocyanate.

If the content of amine droplets in the amine gas stream F1 that enters into the heater is too high, for example, higher than 20 wt %, some of the amine droplets that are not vaporized would be separated from the amine gas stream during the process of heating and vaporization and are combined into a flow which drop and are discharged from the drain port 3. The discharged liquid material F3 can return to the amine vaporizer to revaporize to increase the vaporization rate of amine.

The method for preparing isocyanate using the heater of the present invention will be further illustrated by the following examples.

In the examples, the content of heavy component in the phosgenation reaction liquid is determined by Shimadzu GC2010 gas chromatograph with DB-5 type chromatographic column (FID detector, the temperature of the injection port: 290° C., the column temperature is raised according to the following steps: the temperature is maintained at 160° C. for 1 minute, then it is increased to 300° C. at the rate of 10° C./min and it is maintained at 300° C. for 11 minutes; the temperature of the detector is 320° C.), peak area normalization method is used to obtain the results.

Example 2

The structure of the heater was basically the same as that of example 1, wherein electrical heating wires made of inert silicon carbide conductive materials doped with 2 wt % Ni were used to form the heater body. The heater body was a cylinder stereoscopic network structure with the thickness of 15 cm and a diameter of 40 cm, the hydraulic diameter of the mesh of the stereoscopic network structure was 0.25 mm, the porosity was 97.5%, and the heat exchange area per unit volume was 550 $m^2/m^3$. The cross section of the electrical heating wire that composed the heater body was in the forms of a triangle, and the triangle had a smallest angle with the angularity of 2°. The electrical resistivity of the heater body measured about 500 $\Omega \cdot m$. The heater body was encapsulated in a 316 L stainless steel heater housing, polyethylene sheath sealing pads were used for the sealing insulation packing.

HDA was preheated and vaporized in the amine vaporizer to obtain amine gas stream that contained about 10 wt % amine droplets that were not vaporized. The amine gas stream entered into the heater housing via the amine gas stream inlet of the heater of the present example. The external voltage of the heater body was 12V, the temperature of the heater body was 300° C. The amine gas stream that did not contain droplets and was discharged from the amine gas stream outlet of the heater, and the gas phase phosgene that was preheated to 300° C. were continuously added to the gas phase phosgenation reactor and were reacted under the temperature of 300° C., the absolute pressure of 0.13

MPa, wherein the feed rate of HDA was 100 kg/h, the feed rate of phosgene was 450 kg/h. The obtained reaction products were cooled quickly to 100° C. to 140° C. by a gas jet and absorption device with o-dichlorobenzene used as the solvent, and the reaction liquid that contained the product 1,6-hexamethylene diisocyanate (HDI) was obtained. The results are shown in table 1.

Comparative Example 2

HDA was preheated and vaporized in the amine vaporizer to obtain amine gas stream that contained about 10 wt % amine droplets that were not vaporized, the amine gas stream entered into the phosgenation reactor via an inlet pipe (the inlet pipe is a straight pipe, the same below) and was vaporized in the inlet pipe. The temperature of the inlet pipe was 305° C., the residence time of the amine gas stream in the inlet pipe was 0.3 s. The amine gas stream and the gas phase phosgene that was preheated to 300° C. were continuously added to the gas phase phosgenation reactor and reacted under the temperature of 300° C., the absolute pressure of 0.13 MPa, wherein the feed rate of HDA was 100 kg/h, the feed rate of phosgene was 450 kg/h. The obtained reaction products were cooled quickly to 100° C. to 140° C. by a gas jet and absorption device with o-dichlorobenzene used as the solvent, and the reaction liquid that contained the product HDI was obtained. The results are shown in table 1.

Example 3

The structure of the heater was basically the same as that of example 1, wherein electrical heating wires made of inert silicon carbide conductive materials doped with 2 wt % Ni were used to form the heater body. The heater body was a cylinder stereoscopic network structure with the dimensions as follows: a thickness of 15 cm and a diameter of 40 cm. The hydraulic diameter of the mesh of the stereoscopic network structure was 0.15 mm, the porosity was 98.5%, and the heat exchange area per unit volume was 650 m$^2$/m$^3$. The cross section of the electrical heating wire that composed the heater body was in the form of a convex pentagon, and the convex pentagon had a smallest angle that was 4°. The electrical resistivity of the heater body measured about 500 Ω·m. The heater body was encapsulated in a 316 L stainless steel heater housing, and polyethylene sheath sealing pads were used for the sealing insulation packing.

IPDA was preheated and vaporized in the amine vaporizer to obtain amine gas stream that contained 15 wt % amine droplets that were not vaporized. The amine gas stream entered into the heater housing via the amine gas stream inlet of the heater of the present example. The external voltage of the heater body was 18V, and the temperature of the heater body was 330° C. The amine gas stream that did not contain droplets and was discharged from the amine gas stream outlet of the heater, and the gas phase phosgene that was preheated to 330° C. were continuously added to the gas phase phosgenation reactor and reacted under the temperature of 330° C., the absolute pressure of 0.13 MPa, wherein the feed rate of IPDA was 60 kg/h, the feed rate of phosgene was 150 kg/h. The obtained reaction products were cooled quickly to 100° C. to 140° C. by a gas jet and absorption device with o-dichlorobenzene used as the solvent, and the reaction liquid that contained the product isophorone diisocyanate (IPDI) was obtained. The results are shown in table 1.

Comparative Example 3

IPDA was preheated and vaporized in the amine vaporizer to obtain amine gas stream that contained 15 wt % amine droplets that were not vaporized. The amine gas stream was first passed through the gas liquid separator to decrease the amine droplets that were not vaporized to 5 wt %, then the amine gas stream entered into the phosgenation reactor via the inlet pipe in which remained amine droplets were vaporized. The temperature of the inlet pipe was 330° C., the residence time of the amine gas stream in the inlet pipe was 0.6 s. The amine gas stream and the gas phase phosgene that was preheated to 330° C. were continuously added to the gas phase phosgenation reactor and reacted under the temperature of 330° C., the absolute pressure of 0.13 MPa, wherein the feed rate of IPDA was 60 kg/h, the feed rate of phosgene was 150 kg/h. The obtained reaction products were cooled quickly to 100° C. to 140° C. by a gas jet and absorption device with o-dichlorobenzene used as the solvent, and the reaction liquid that contained the product IPDI was obtained. The results are shown in table 1.

Example 4

The structure of the heater was basically the same as that of example 1, wherein electrical heating wires made of inert silicon carbide conductive materials doped with 2 wt % Ni were used in the heater body. The heater body was a cylinder stereoscopic network structure with the dimensions as follows: a thickness of 15 cm and a diameter of 40 cm. The hydraulic diameter of the mesh of the stereoscopic network structure was 0.15 mm, the porosity was 98.5%, and the heat exchange area per unit volume was 650 m$^2$/m$^3$. The cross section of the electrical heating wires that composed the heater body was in the form of a convex quadrilateral, and the convex quadrilateral had a smallest angle with the angularity of 5°. The electrical resistivity of the heater body measured about 500 Ω·m. The heater body was encapsulated in a 316 L stainless steel heater housing, and polyethylene sheath sealing pads were used for the sealing insulation packing.

TDA was preheated and vaporized in the amine vaporizer to obtain amine gas stream that contained 10 wt % amine droplets that were not vaporized. The amine gas stream entered into the heater housing via the amine gas stream inlet of the heater of the present example. The external voltage of the heater body was 24V, and the temperature of the heater body was 330° C. The amine gas stream that did not contain droplets and was discharged from the amine gas stream outlet of the heater, and the gas phase phosgene that was preheated to 320° C. were continuously added to the gas phase phosgenation reactor and reacted under the temperature of 350° C., the absolute pressure of 0.15 MPa, wherein the feed rate of TDA was 50 kg/h, the feed rate of phosgene was 200 kg/h. The obtained reaction products were cooled quickly to 100° C. to 140° C. by a gas jet and absorption device with toluene used as the solvent, the reaction liquid that contained the product toluene diisocynate (TDI) was obtained. The results are shown in table 1.

Comparative Example 4

TDA was preheated and vaporized in the amine vaporizer to obtain amine gas stream that contained 10 wt % amine droplets that were not vaporized. The amine gas stream entered into the phosgenation reactor via the inlet pipe in which the amine droplets were vaporized. The temperature of the inlet pipe was 310° C., the residence time of the amine gas stream in the inlet pipe was 0.5 s. The amine gas stream and the gas phase phosgene that was preheated to 320° C. were continuously added to the gas phase phosgenation reactor and reacted under the temperature of 350° C., the absolute pressure of 0.15 MPa, wherein the feed rate of TDA was 50 kg/h, the feed rate of phosgene was 200 kg/h. The obtained reaction products were cooled quickly to 100° C. to 140° C. by a gas jet and absorption device with o-dichlorobenzene used as the solvent, and the reaction liquid that contained the product TDI was obtained. The results are shown in table 1.

Example 5

The structure of the heater was basically the same as that of example 1, wherein electrical heating wires made of inert silicon carbide conductive materials doped with 2 wt % Ni were used in the heater body. The heater body was a cylinder stereoscopic network structure with the dimensions as follows: a thickness of 15 cm and a diameter of 40 cm. The hydraulic diameter of the mesh of the stereoscopic network structure was 0.35 mm, the porosity was 98.5%, and the heat exchange area per unit volume was 650 $m^2/m^3$. The cross section of the electrical heating wires that composed the heater body was in the form of a sector, and the central angle of the sector was 3°. The electrical resistivity of the heater body measured about 500 $\Omega \cdot m$. The heater body was encapsulated in a 316 L stainless steel heater housing, and polyethylene sheath sealing pads were used for the sealing insulation packing.

TDA was preheated and vaporized in the amine vaporizer to obtain amine gas stream that contained 10 wt % amine droplets that were not vaporized. The amine gas stream entered into the heater housing via the amine gas stream inlet of the heater of the present example. The external voltage of the heater body was 24V, and the temperature of the heater body was 330° C. The amine gas stream that did not contain droplets and was discharged from the amine gas stream outlet of the heater, and the gas phase phosgene that was preheated to 320° C. were continuously added to the gas phase phosgenation reactor and reacted under the temperature of 350° C., the absolute pressure of 0.15 MPa, wherein the feed rate of TDA was 50 kg/h, the feed rate of phosgene was 200 kg/h. The obtained reaction products were cooled quickly to 100° C. to 140° C. by a gas jet and absorption device with toluene used as the solvent, and the reaction liquid that contained the product toluene diisocynate (TDI) was obtained. The results are shown in table 1.

Example 6

The structure of the heater was basically the same as that of example 1, wherein electrical heating wires made of inert silicon carbide conductive materials doped with 1 wt % Ni were used in the heater body. The heater body was a cylinder stereoscopic network structure with the dimensions as follows: a thickness of 15 cm and a diameter of 40 cm. The hydraulic diameter of the mesh of the stereoscopic network structure was 0.15 mm, the porosity was 98.5%, and the heat exchange area per unit volume was 850 $m^2/m^3$. The cross section of the electrical heating wires that composed the heater body was in the form of an arch, and the radian of the arch was 5°. The electrical resistivity of the heater body measured about 600 $\Omega \cdot m$. The heater body was encapsulated in a 316 L stainless steel heater housing, polyethylene sheath sealing pads were used for the sealing insulation packing.

IPDA was preheated and vaporized in the amine vaporizer to obtain amine gas stream that contained 15 wt % amine droplets that were not vaporized. The amine gas stream entered into the heater housing via the amine gas stream inlet of the heater of the present example. The external voltage of the heater body was 16V, and the temperature of the heater body was 330° C. The amine gas stream that did not contain droplets and was discharged from the amine gas stream outlet of the heater, and the gas phase phosgene that was preheated to 330° C. were continuously added to the gas phase phosgenation reactor and reacted under the temperature of 330° C., the absolute pressure of 0.13 MPa, wherein the feed rate of IPDA was 60 kg/h, the feed rate of phosgene was 150 kg/h. The obtained reaction products were cooled quickly to 100° C. to 140° C. by a gas jet and absorption device with o-dichlorobenzene used as the solvent, and the reaction liquid that contained the product IPDI was obtained. The results are shown in table 1.

TABLE 1

The comparison of the technical effects of examples 2-6 and comparative examples 2-4

|  | Pressure loss (KPa) | Running period (h) | The content of the heavy component in the reaction liquid (A/A %) |
|---|---|---|---|
| Example 2 | 0.5 | 2280 | 0.6 |
| Comparative example 2 | 0.4 | 1296 | 1.9 |
| Example 3 | 0.6 | 2250 | 0.7 |
| Comparative example 3 | 8.9 | 1574 | 2.5 |
| Example 4 | 0.6 | 2550 | 0.4 |
| Comparative example 4 | 0.5 | 1274 | 2.1 |
| Example 5 | 0.7 | 2790 | 0.5 |
| Example 6 | 0.8 | 2990 | 0.6 |

* The pressure loss is the pressure drop inside the heater.

From the results of table 1, it can be seen that comparing with the comparative examples, after the heaters of the examples of the present invention were used, the running periods of the device, from the vaporization of the amine to the phosgenation reaction, were prolonged, and the contents of the heavy component impurities in the reaction liquid were significantly decreased.

The invention claimed is:

1. A heater for heating and vaporizing droplets in a gas stream, comprising a heater housing and a heater body located inside the heater housing, the heater housing is provided with an airflow inlet, a drain port and an airflow outlet, wherein the airflow inlet is provided on the side wall of the heater housing, the airflow outlet is provided on the top of the heater housing, and the drain port is provided at the bottom of the heater housing; an airflow enters into the heater housing via the airflow inlet, flows through the heater body, and then is discharged via the airflow outlet; the heater body consists of one or more stereoscopic network structures formed by interweaving one or more electrical heating wires and is in form of a cylinder shape with a height-to-diameter ratio of the heater body is 1:1-10;
   wherein, a cross section of the electrical heating wire is in a shape of an arch; wherein, a central angle corresponding to an arc of the arch is 1°-10°; and
   wherein, the gas stream is an amine gas stream, and the droplets are amine droplets.

2. The heater according to claim 1, wherein the stereoscopic network structure formed by interweaving electrical heating wires is combined with the inner wall of the heater housing through sealing insulation packing.

3. The heater according to claim 2, wherein the hydraulic diameter of the mesh of the stereoscopic network structure is smaller than 1 mm.

4. The heater according to claim 3, wherein the porosity of the stereoscopic network structure is 75-99.5%.

5. The heater according to claim 4, wherein the heat exchange area per unit volume of the stereoscopic network structure is 100-1000m2/m3.

6. The heater according to claim 3, wherein the hydraulic diameter of the mesh of the stereoscopic network structure is 0.01-0.25 mm, and the porosity of the stereoscopic network structure is 90-99.5%.

7. A method for preparing isocyanate, comprising:
   (1) vaporizing amine into an amine gas stream that contains amine droplets;
   (2) eliminating the amine droplets contained in the amine gas stream to obtain an amine gas stream that contains amine droplets lower than 0.1 wt. %;
   (3) allowing a gas phase phosgenation reaction to be carried out between the amine gas stream that contains amine droplets lower than 0.1 wt. % and phosgene to obtain isocyanate;
   wherein in step (2), the heater according to claim 1 is used to eliminate the amine droplets in the amine gas stream.

* * * * *